United States Patent [19]
Azer et al.

[11] Patent Number: 5,490,852
[45] Date of Patent: Feb. 13, 1996

[54] ORTHOPEDIC AWL

[76] Inventors: Samir N. Azer, 9335 Mt. Vernon Cir., Alexandria, Va. 22309; William R. Krause, 820 Gilliams Mountain Rd., Charlottesville, Va. 22903

[21] Appl. No.: 197,078

[22] Filed: Feb. 16, 1994

[51] Int. Cl.6 .................................. A61B 17/16
[52] U.S. Cl. .............................. 606/79; 606/80
[58] Field of Search ................ 606/79, 80, 84, 606/185; D8/47; 30/366; 81/28

[56] References Cited

U.S. PATENT DOCUMENTS

| | | | |
|---|---|---|---|
| 884,856 | 4/1908 | Réquillart | 81/35 |
| 930,477 | 8/1909 | Hudson | 606/80 |
| 1,923,177 | 8/1933 | Tucker | 606/80 |
| 4,342,309 | 8/1982 | Eftekhar | 606/80 |
| 5,098,433 | 3/1992 | Stednitz et al. | 606/79 |
| 5,306,301 | 4/1994 | Graf et al. | 606/72 |

*Primary Examiner*—Tamara L. Graysay
*Assistant Examiner*—Scott B. Markow
*Attorney, Agent, or Firm*—Sheldon H. Parker

[57] ABSTRACT

An awl for providing entry into and subsequent penetration of a bone is disclosed. The awl features a first section which is straight and has a first end, an exterior end, and a cutting tip at its exterior end. The second section of the awl is a connection region which has a first end and a second end. The first end of the second section extends essentially normal from the first end of the first section. The third section provides an external reference for the direction of the cutting tip and extends from the second end of the second section in a direction essentially parallel to the first section, such that the orienation of the third section represents the orienation of the first section.

2 Claims, 3 Drawing Sheets

ORTHOPEDIC AWL

FIELD OF INVENTION

The present invention relates to orthopedic devices, and more particularly, to an orthopedic device commonly known as an awl which is used during intramedullary nailing, i.e., a surgical procedure for creating an opening in a bone into which certain devices can be introduced.

BACKGROUND OF THE INVENTION

In the past, various procedures for creating an opening (also referred to as an entry hole or portal) in a bone to allow inserting pins, rods, or other devices into the medullary canal required the use of drills, reamers, or curved awls. Since typical drills and reamers are essentially straight, a surgeon attempting to use one of these devices would tend to drive it off center because the patient's torso prevents access to the center of the medullary canal. In addition, the length of the drill or reamer also prevents the surgeon from sufficient maneuverability without the patient's torso interfering with drill placement. Recently, the use of curved awls has emerged as the prevalent paractice, but although their use overcomes some of the disadvantages associated with using a drill or reamer, their use still presents a difficulty in ensuring that the entry hole is correctly placed.

Determining an appropriate entry point on the surface of a bone, e.g., the femur, into which the nail can be inserted, and then executing entry at that point, is a critical step in the process of closed intramedullary nailing. In the past, surgeons have reccommended entering the femur at the tip of the greater trochanter because of particular problems which can result from attempting to enter at a more centralized location. These potential problems include: 1) damage to the femoral head blood supply, 2) femoral neck fracture, and 3) septic arthritis. Entry through the greater trochanter, however, was found to lead to eccentric reaming, which in turn caused 1) thinning, and often comminution, of the medial cortex (i.e., fracturing it into small fragments), 2) various deformations of the proximal fragment, and 3) fracture of the greater trochanter. In one study of 143 cases in which entry at the greater trochanteric was performed, femoral neck fracture occurred in 3% of the patients and comminution of the proximal fragment occurred in another 3%.

Others have proposed that the pyriformis fossa offered a more anatomically appropriate entry site because the pyriformis fossa is centered over the axis of the medullary canal. Based on radiographs and the use of an interactive graphics program, still others have recommended that the area at the junction of the femoral neck and the greater trochanter slightly anterior to or in the pyriformis fossa offers the most appropriate entry point. A study of the use of this procedure (referred to as anterior insertion of the nail), however, reported that proximal fragment comminution occurred in 26% of the cases. From the standpoint of biomechanics, a posteriorly placed entry point in the pyriformis fossa generated the least stresses in the femur. Consequently, a posteriorly placed entry portal, medial to the greater trochanter, has become the position recommended for entry position.

Since the conception of closed intramedullary fixation, various instruments as described above have been used for creating the entry hole. Recently, curved awls have emerged as the most widely used instruments in this procedure. These awls are shaped with a curved and pointed tip which is attached to a serpentine handle configured in the form of a "shepard's crook" as shown in FIG. 1. Several minor but significant problems follow from the use of a curved awl in the closed intramedullary fixation procedure.

First, as the pointed tip is inserted into the proximal femur, the tip is oriented and pushed towards the medial wall of the femur as shown in FIG. 2. If the tip is inserted too far, it will penetrate and violate the medial wall of the femur, causing an unwanted fracture of the bone. Moreover, the trochanter can fracture if the awl is inserted too aggressively.

Second, in order to centralize the entry hole for connecting it with the intramedullary canal of the bone and inserting devices, the point of the awl must be rotated laterally. This motion causes increased destruction of the internal bone structure and enlarges the entry hole. While the patient is disposed in a supine position, the interference of the handle of the awl with the patient's torso prevents the surgeon from laterally rotating the awl to centralize the tip while it is inserted in the bone as shown in FIG. 2.

Third, the cavity created by the awl is insufficiently deep to allow the alignment guide wire to be directly inserted into the medullary canal because the remaining cancellous bone structure tends to deflect the guide wire away from the central axis of the femur.

Moreover, the configuration of the presently available curved awl fails to offer the surgeon any readily ascertainable points of reference to guide her use of the device once the tip has been inserted and is no longer visible. In other words, determining whether the tip of a curved awl is being inserted in alignment with the medullary canal becomes difficult after the tip has been inserted. In addition, the configuration of the curved awl fails to provide any surface directly aligned with the point onto which a surgeon can apply pressure for positively and predictably transmitting a point force to the tip to facillitate creating an entry hole. In other words, striking or exerting force on a curved awl may result in further complications because the force may not be transmitted in alignment with the desired direction of tip travel.

It would be advantageous to provide a device for creating a entry hole in a bone during a surgical procedure (e.g. closed intramedullary fixation) that would ensure correct placement of the hole.

It would also be advantageous to provide a device which would permit a surgeon to manipulate it during use without interference from the patient's torso.

It would also be advantageous to provide a device in a configuration that would offer the surgeon using the device, points of reference for judging the position of the tip of the device with respect to the handle of the device.

It would also be advantageous to provide a device in a configuration that would allow the surgeon using it to transmit force to the tip of the device by applying pressure directly above the tip.

SUMMARY OF THE INVENTION

According to the method of the invention, an orthopaedic awl for ease of insertion and entry into long bones will be described. The awl allows for a straight approach into the intramedullary canal from the pyriformis fossa, an external orientation and reference for the direction the pointed tip is positioned within bone, and a handle positioned so as to allow complete manipulation of the awl and not contact the patient.

Entry in the region of the pyriformis fossa is made just medial to the greater trochanter and posterior to the central axis of the femoral neck. The orientation of the cutting tip is directed towards the central axis of the femur from visualization of the external handle. The awl is inserted and advanced with a slight rotating motion to cut the cortex and enlarge the entry hole. Lateral and anterior-posterior fluoroscopy are used to confirm central placement. During imaging, the awl can be rotated out of the direct field without disturbing the orientation of the cutting tip. The straight cutting tip prevents deflection from the cancellous network within the trochanteric region to provide a centrally located canal for instrument passage.

BRIEF DESCRIPTION OF THE DRAWINGS

The objects and features of the present invention will become more fully apparent once considered in view of the following detailed description and the drawings, wherein:

FIG. 6b is a side view of the tip of FIG. 6a;

FIG. 6c illustrates an end view of a slotted tip for use with the instant invention;

DETAILED DESCRIPTION OF THE PREFERRED INVENTION

Figure 1:
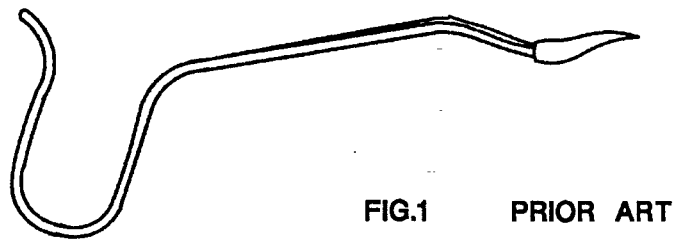
FIG. 1 depicts a pictorial view of a prior art awl with the curved cutting tip and offset handle.
Figure 2:
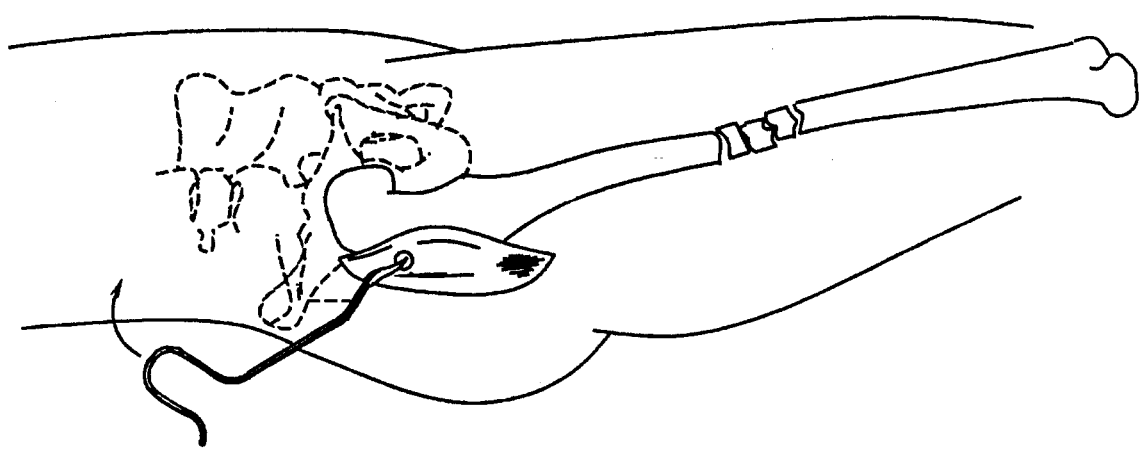
FIG. 2 depicts the prior art awl positioned for entry into the femur with the cutting tip directed towards the medial wall of the femur and how the torso of the patient interferes with centering the cutting tip.

In describing a preferred embodiment of the present invention as illustrated in the drawings, specific terminology will be used for the sake of clarity. The present invention, however, is not intended to be limited to the specific terms so selected, and it is understood that each term includes all technical equivalents which operate in a similar manner to accomplish a similar task.

Figures 3, 4:
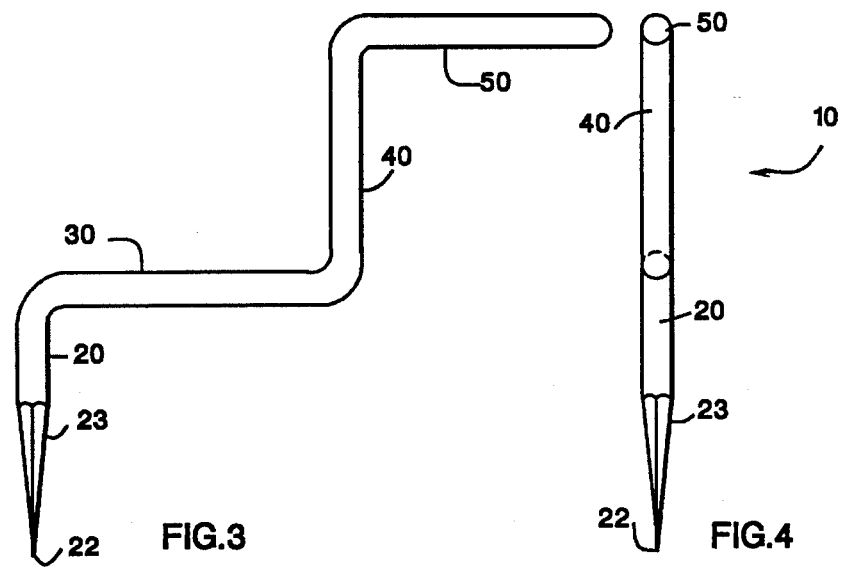
FIG. 3 depicts a top view of the present invention.
FIG. 4 depicts the corresponding side view of the present invention.

Referring to the drawings generally, and in particular to FIGS. 3 and 4, the awl of the present invention is shown as indicated generally by reference numeral 10. The awl 10 includes an insertion portion 20, a medial-lateral reference arm 30, an anterior-posterior arm 40, and a handle 50.

Figure 5:
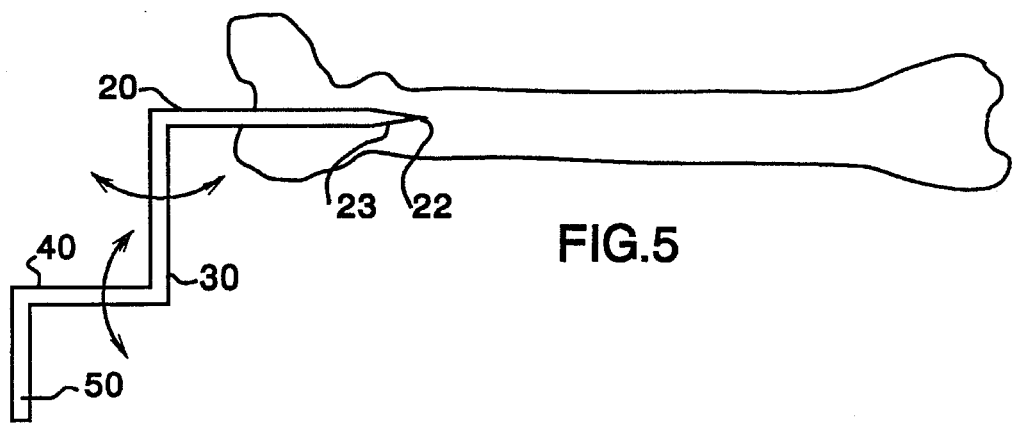
FIG. 5 depicts a schematic view show the intended use of the present invention in entering the femur; 6a illustrates an end view of a cannulated tip for use with the instant invention.

The insertion portion 20 is comprised of a cutting tip 22 and a tip extension 23. The cutting tip 22 is of a cannulated, slatted or fluted configuration as shown in FIGS. 6a–6f, to permit penetrating and cutting the bone material. The tip extension 23 provides for the cutting tip 22 to enter the bone and extend the opening into the intramedullary canal of the bone as illustrated in FIG. 5.

The medial-lateral reference arm 30 is positioned at 90 degrees with respect to the insertion portion 20. The medial-lateral arm 30 provides a reference to the surgeon as to the medial-lateral direction of the insertion portion 20 when it is positioned within the bone.

The anterior-posterior arm 40 is positioned 90 degrees with respect to the medial-lateral arm 30 and parallel to the insertion portion 20. The anterior-posterior arm 40 provides a reference to the user as to the anterior-posterior direction of the insertion portion 20 when it is positioned within the bone.

Figure 7:
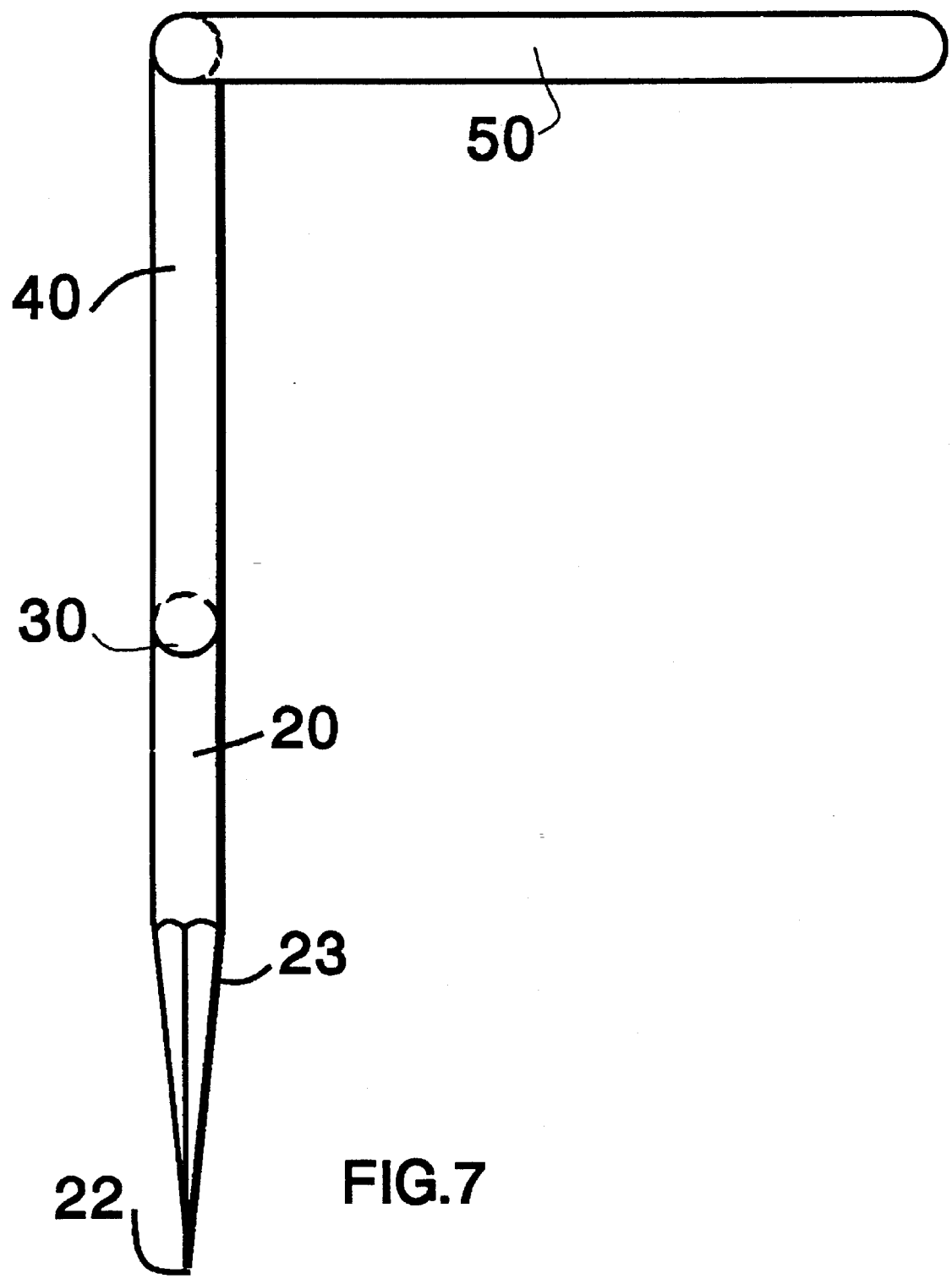
FIG. 7 depicts an alternative embodiment of the configuration of the handle.

The handle 50 is preferably positioned at a 90 degree angle with respect to the anterior-posterior arm 40 in a direction suitable for the application. The preferred orientation of the handle would be 90 degrees with respect to the anterior-posterior arm 40 and parallel to the medial-lateral arm 30, or 90 degrees with respect to both the anterior-posterior arm 40 and the medial-lateral arm 30 as shown in FIG. 7.

Figure 6A:
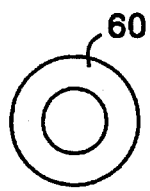
Figure 6B:
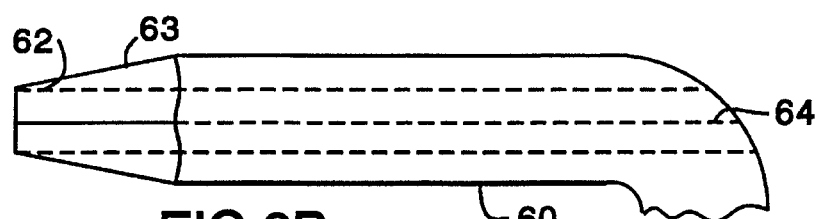
Figure 6B:
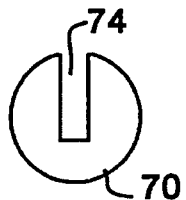

In FIGS. 6a–f illustration examples of the type of tip extensions 63 which can be utilized with the instant device. FIGS. 6a and 6b show the side and end view of the cannulated insertion portion 60. The cannulated insert portion 60 is provided with an interior channel 64 which runs the length of the tip extension 63 and exits at the cutting tip 62.

Figure 6D:
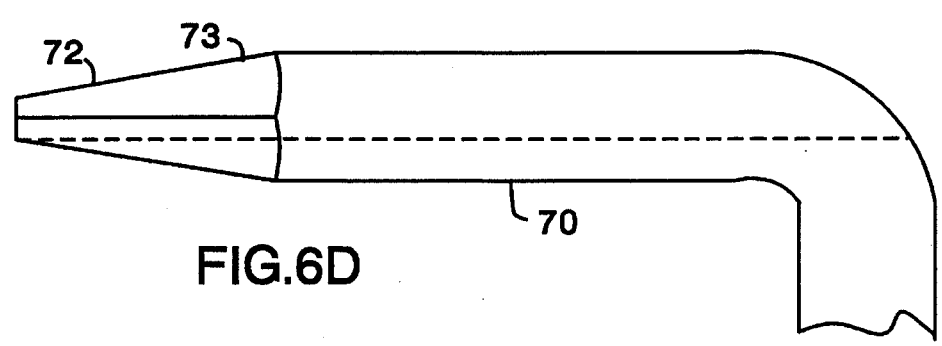
FIG. 6d is a side view of the tip of FIG. 6c.

In FIGS. 6c and 6d the insertion portion 70 is slotted at the tip extension 73. The slot 74 extends the length of the tip extension 73 to the cutting tip 72.

Figure 6E:
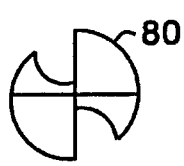
FIG. 6e illustrates an end view of a fluted tip for use with the instant invention.
Figure 6F:
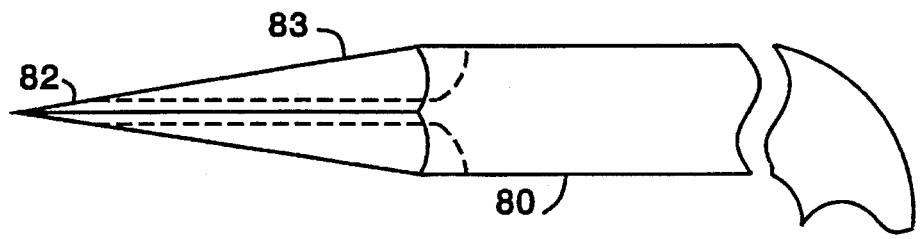
FIG. 6f is a side view of the tip of FIG. 6e.

In FIGS. 6e and 6f, the extension tip 83 of insertion portion 80 is provided with a fluted configuration.

In the preferred embodiment, the awl 10 is constructed of surgical grade steel or similar surgically acceptable material. The bend radii located at the points where the various segments join are 0.25 in. All other design considerations are well known to those with skill in the art of fabricating surgical instruments.

Prior to the use of the awl 10 in a surgical procedure, e.g. the closed intramedullary fixation of a femur, the surgeon makes an incision in the patient's leg to allow access to the femur. Lateral and anterior-posterior fluoroscopy are used to confirm the perceived central placement. During imaging, the awl 10 can be rotated out of the direct field without disturbing the orientation of the cutting tip extension 23, of the insertion portion 20. Entry into the region of the pyriformis fossa is made just medial to the greater trochanter and posterior to the central axis of the femoral neck. The orientation of the cutting tip 22 is directed towards the central axis of the femur by maintaining a parallel relationship between the insertion portion 20 and the handle 50. The awl 10 may be manipulated to achieve the proper orientation without contacting the patient. The awl 10 is inserted further by rotating it slightly to allow it to cut the cortex and enlarge the entry hole. The stiffness and straight configuration of the cutting tip 22 prevent the awl 10 from deflecting the cancellous network within the trochanteric region, thereby providing a centrally located canal for passing guide wires. If the surgeon encounters resistance to penetration during the procedure, the medial-lateral arm 30 can be tapped to facillitate penetration of the cutting tip 22.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention. D2 In FIGS. 6a-f illustration examples of the type of tip extensions 63 which can be utilized with the instant device. FIGS. 6a and 6b show the side and end view of the cannulated insertion portion 60. The cannulated insert portion 60 is provided with an interior channel 64 which runs the length of the tip extension 63 and exits at the cutting tip 62.

In FIGS. 6c and 6d the insertion portion 70 is slotted at the tip extension 73. The slot 74 extends the length of the tip extension 73 to the cutting tip 72.

In FIGS. 6e and 6f, the extension tip 83 of insertion portion 80 is provided with a fluted configuration.

What is claimed is:

1. An awl for providing an entry hole into a bone and subsequent penetration of the awl into said bone, said awl being a unitary structure comprising:

a first section, said first section being substantially an elongated member having a longitudinal axis, and having
 a first end and
 an exterior end, said exterior end having a cutting tip, a second section, said second section being an elongated member having a first end and
 a second end, said second end being integral with said first end of said first section, said first end of said second section and extending approximately normal from said first section, a third section, said third section being an elongated member having a longitudinal axis, said first section, said second section and said third section lying in a first plane, said third section having
 a first end, integral with said first end of said second section, and
 a second end, said longitudinal axis of said third section being parallel to said longitudinal axis of said first section, said third section providing an external reference for the orientation of said cutting tip, a fourth section, said fourth section lying in said first plane and having
 a first end, integral with said third section second end, and
 a second end, directed away from said longitudinal axis of said first section, said fourth section forming an angle of approximately 90 degrees with said third section, whereby the orientation of said third section represents the orientation of said first section and said fourth section is a hand hold section.

2. An awl for providing an entry hole into a bone and subsequent penetration of the awl into said bone, said awl being a unitary structure comprising:

a first section, said first section being substantially an elongated member having a longitudinal axis, and having
 a first end and
 an exterior end, said exterior end having a cutting tip, a second section, said second section being an elongated member having a first end and
 a second end, said second end being integral with said first end of said first section, said first end of said second section and extending approximately normal from said first section, a third section, said third section being an elongated member having a longitudinal axis, said first section, said second section and said third section lying in a first plane, said third section having
 a first end, integral with said first end of said second section, and
 a second end, said longitudinal axis of said third section being parallel to said longitudinal axis of said first section, said third section providing an external reference for the orientation of said cutting tip, a fourth section, said fourth section lying in a second plane which is normal to said first plane, and having
 a first end, integral with said third section second end, and
 a second end, directed away from said longitudinal axis of said first section, said fourth section forming an angle of approximately 90 degrees with said third section, whereby the orientation of said third section represents the orientation of said first section and said fourth section is a hand hold section.

* * * * *